United States Patent [19]

Fenoglio

[11] Patent Number: 4,908,145
[45] Date of Patent: Mar. 13, 1990

[54] ENGINE SEAL COMPATIBLE DISPERSANTS FOR LUBRICATING OILS

[75] Inventor: David J. Fenoglio, Wheaton, Ill.

[73] Assignee: Amoco Corporation, Chicago, Ill.

[21] Appl. No.: 103,169

[22] Filed: Sep. 30, 1987

[51] Int. Cl.$^4$ .......................................... C10M 105/22
[52] U.S. Cl. ................... 252/51.5 A; 252/51; 252/356; 252/357
[58] Field of Search ............... 252/51.5 A, 47.5, 50, 252/51, 51.5 R, 386, 387

[56] References Cited

U.S. PATENT DOCUMENTS

| | | | |
|---|---|---|---|
| 3,272,746 | 9/1966 | LeSner | 252/51.5 A |
| 3,338,832 | 8/1967 | LeSner | 252/47.5 |
| 3,341,542 | 9/1967 | LeSner | 252/51.5 A |
| 3,869,394 | 3/1975 | Daniels | 252/50 X |
| 4,111,822 | 9/1978 | Caruso | 252/51.5 A |
| 4,257,779 | 3/1981 | Sung | 252/51.5 A X |
| 4,263,015 | 4/1981 | Sung | 252/51.5 A X |
| 4,283,296 | 8/1981 | Nebzydoski | 252/51.5 A X |
| 4,379,064 | 4/1983 | Cengel | 252/51.5 A |
| 4,491,527 | 1/1985 | Lange | 252/51.5 A |

Primary Examiner—William R. Dixon, Jr.
Assistant Examiner—James M. Hunter, Jr.
Attorney, Agent, or Firm—Matthew R. Hooper; William H. Magidson; Ralph C. Medhurst

[57] ABSTRACT

There is provided a process for preparing an oil-soluble composition that is suitable for use as a dispersant in lubricating oils, is compatible with fluorohydrocarbon elastomers, and is rich in alkyl bis-3-amino-1,2,4-triazole. Selected conditions are necessary to produce a reaction product that is compatible with fluorohydrocarbon elastomers.

There is provided also a lubricating oil composition which comprises the aforesaid dispersant.

13 Claims, No Drawings

ENGINE SEAL COMPATIBLE DISPERSANTS FOR LUBRICATING OILS

BACKGROUND OF THE INVENTION

1. Field of the Invention

This invention relates to lubricating oil additive compositions which provide effective dispersant performance coupled with minimal attack upon fluorohydrocarbon-type engine seals and lubricating oil compositions containing said additive compositions. More particularly, this invention relates to lubricating oil dispersant additive compositions prepared by reacting substituted succinic acid or derivatives thereof with a basic salt of aminoguanidine under selected conditions and lubricating oil compositions containing said dispersant additive compositions.

2. Description of the Prior Art

The presence of water and precursors of sludge in lubricating oils constitutes a very serious problem that is associated with crankcase lubricating oils. There occurs in the lubricating oil various foreign particles, such as dirt, soot, and products of decomposition that result from the breakdown of the lubricating oil. The combination of water and such foreign particles results in the deposition of sludge which has a deleterious effect upon the efficient operation of the engine containing the lubricating oil. In order to prevent the deposition of sludge, various detergents and dispersants are added to the lubricating oil composition.

Today, flexible engine seals comprising fluorohydrocarbon compositions are being used in assembling internal combustion engines. These seals are used to prevent leakage of lubricants at those points where moving parts, such as crankshafts, leave the engine. Of course, any appreciable leak of the lubricant from the internal combustion crankcase is very undesirable. Consequently, an important consideration when selecting the dispersants for use in the lubricating oil composition, in addition to maintaining the cleanliness of the engine, is their compatibility with fluorohydrocarbon crankshaft seals and clutch plate liners in transmissions. These seals comprise fluorohydrocarbon elastomers which are often attacked by the dispersant. For example, Mannich dispersants are incompatible with such fluorohydrocarbon-type engine seals.

In U.S. Pat. No. 4,379,064, Cengel, et al., disclosed the passivating of basically reacting polyamine dispersants to fluorohydrocarbon compositions that are employed in internal combustion engines by the mild oxidation of such polyamine dispersants.

In U.S. Pat. Nos. 3,272,746 and 3,341,542, Le Suer, et al., disclose lubricating oil compositions containing acylated nitrogen compounds prepared, for example, by reacting a substituted succinic acid or derivative thereof with a nitrogen-containing compound, such as ammonia, aliphatic amines, aromatic amines, heterocyclic amines, or carboxylic amines. The resulting detergent composition comprises an oil-soluble, acylated nitrogen composition characterized by the presence within its structure of (A) a substantially hydrocarbon-substituted polar group selected from the class consisting of acyl, acylimidoyl, and acyloxy radicals wherein the substantially hydrocarbon substituent contains a least about 50 aliphatic carbon atoms and (B) a nitrogen-containing group characterized by a nitrogen atom attached directly to said relatively polar group. In Example 38 of these patents, polyisobutene-substituted succinic anhydride, aminoguanidine bicarbonate, and mineral oil were mixed and heated at a temperature of 130° C. (266° F.) to 165° C. (329° F.) for 5 hours. The residue was mixed with mineral oil and heated to 150° C. (302° F.) and filtered. The resulting product was used as a lubricating oil additive and found to be an effective dispersant. These patents teach that the mixture of acid-producing compound and the nitrogen-containing reactant is usually heated at a temperature above about 80° C. (176° F.), preferably within the range of about 100° C. (212° F.) to about 250° C. (482° F.). The patents teach that guanidines are included in sources of nitrogen-containing compounds and present, as examples, guanidine, 1,3-diphenylguanidine, and 1,2,3-tributylguanidine. These patents do not indicate that the resulting product comprises triazoles. Furthermore, there is no suggestion that the dispersants prepared according to the disclosure of these patents would be either deleterious to or compatible with certain types of engine seals, e.g., seals comprising fluorohydrocarbon elastomers. The disclosure is too ambiguous and too broad to teach the present invention.

In U.S. Pat. No. 4,491,527, Lange, et al., disclose ester-heterocycle compositions useful as "lead paint" inhibitors and lubricants, e.g., compositions comprising a major proportion of a pentaerythritol ester of an alkenyl succinic acid in which the alkenyl group contains at least about 30 carbon atoms and a minor proportion of a heterocyclic condensation product of said alkenyl succinic acid derived from a 5-membered ring heterocycle containing at least 2 ring hetero atoms separated by a single carbon atom, at least one of said hetero atoms being nitrogen. The heterocyclic condensation product is characterized by the presence of at least one heterocyclic moiety including a 5- or 6-membered ring which contains at least 2 ring hetero atoms, separated by a single carbon atom. Such ring hetero atoms may be oxygen, sulfur, and nitrogen, with at least one thereof being nitrogen. Most often, the heterocyclic moiety contains a maximum of three hetero atoms and a 5-membered ring, preferably, a triazole or thiadiazole ring, and, most desirably, a 1,2,4-triazole ring. This patent teaches that aminoguanidine and salts of aminoguanidine, such as aminoguanidine bicarbonate, are examples of acyclic heterocycle precursors which may be reacted with the proper acid or acid derivative group. This patent does not suggest that a fluorohydrocarbon-type engine seal would be compatible with such ester-heterocycle composition that is prepared by the method disclosed in this patent.

It has not been found that a lubricating oil dispersant additive composition can be prepared by reacting an alkyl-substituted dicarboxylic acid compound, such as an alkyl-substituted succinic acid or acid anhydride, with a basic salt of aminoguanidine under selected conditions and that the resulting product comprising alkyl bis-3-amino-1,2,4-triazole will perform acceptably as a lubricating oil dispersant and will be compatible with engine seals made of flourohydrocarbon elastomers.

SUMMARY OF THE INVENTION

According to the present invention, there is provided an improved process for preparing an oil-soluble composition which can be used suitably as a dispersant additive for lubricating oils wherein an alkyl-substituted dicarboxylic acid compound, such as a polybutenyl succinic acid compound, is reacted with a basic salt of aminoguanidine to provide a product that is rich in alkyl bis-3-amino-1,2,4-triazole, e.g., a polybutenyl bis-3-amino-1,3,4-triazole, and that is compatible with fluorohydrocarbon elastomers. The reaction is carried out typically at atmospheric pressure and a temperature that is within the range of about 155° C. (311° F.) to about 200° C. (392° F.) and at a ratio of moles of aminoguanidine compound per mole of acid producing compound that is within the range of about 1.6:1 to about 2:1.

There is provided also a lubricating oil composition which comprises the aforesaid dispersant.

DESCRIPTION AND PREFERRED EMBODIMENTS

As pointed out hereinabove, sludge which forms in a lubricating oil in an internal combustion engine deleteriously effects performance of the engine. Detergents and dispersants can be added to the lubricating oil to maintain cleanliness in the engine and to minimize deposition of sludge. However, such dispersants sometimes provide a disadvantage. For example, polyamine dispersants are dispersants are incompatible with the more recent flexible engine seals that are made up of fluorohydrocarbon compositions. These seals suitably prevent leakage of lubricants from the engine at points where moving parts, such as crankshafts, leave the engine. However, if engine seals that are prepared from fluorohydrocarbon compositions are utilized to seal engines containing lubricating oils having polyamine dispersants, the seals will be affected deleteriously by such dispersants. Mechanical deterioration, dimensional deterioration, discoloration, crazing, and swelling of the seals occur. The polyamine-containing dispersants interact with the fluorohydrocarbon seals to alter the underlying polymeric structure. The composition of the seal absorbs oil and as the oil content of the seal increases the mechanical strength and dimensional integrity of the seal deteriorate to such an extent that the seal does not prevent leakage of lubricant from the crankcase.

There are various types of dispersants. For example, reaction products of a monocarboxylic acid, a dicarboxylic acid, a polycarboxylic acid, or derivatives thereof, with nitrogen-containing compounds, such as amines, are described in numerous patents. Examples of such patents are U.S. Pat. Nos. 3163,603; 3,184,474; 3,215,707; 3,219,666; 3,271,310; and 3,272,746. Such reaction products are identified hereinafter as carboxylic polyamine dispersants.

There are those dispersants which comprise reaction products of alicyclic halides containing at least about 40 carbon atoms with amines, preferably, polyalkylene polyamines, examples of which dispersants are described in U.S. Pat. Nos. 3,275,554; 3,438,757; 3,454,555; and 3,565,804. Such dispersants can be identified as alkyl polyamine dispersants.

A third type of dispersant comprises the reaction products of an alkyl phenol or an oxidized olefinic polymer, wherein the alkyl group is oil soluble, with aliphatic aldehydes containing 1 through 7 carbon atoms and amines, particularly alkylene polyamines. Such dispersants can be identified as Mannich polyamine dispersants and are described in such prior art at U.S. Pat. Nos. 2,459,112; 3,036,003; 3,355,270; 3,461,172; 3,442,808; 3,459,661; 3,544,470; 3,,697,574; 3,591,598; 3,649,229; 3,726,882; and 4,011,380.

Another type of dispersant comprises polymers containing an oil-solubilizing group, e.g., a pendant alkyl group having at least about 8 carbon atoms, and a polar group, e.g., interpolymers of decyl methacrylate, vinyl decyl ether, or a relatively high molecular weight olefin with aminoalkyl acrylates, aminoalkyl acrylamides or poly(oxyalkalene)-substituted alkyl acrylates, as well as copolymers of styrene, alkyl maleates, and maleic acid amides or imides, respectively. Such polymers can be identified as polymeric polyamine dispersants and are exemplified in U.S. Pat. Nos. 3,329,658; 3,449,250; 3,519,565; 3,666,730; 3,687,849; and 3,702,300.

Another type of dispersant comprises products obtained by post-treating the carboxylic polyamine, alkyl polyamine, Mannich polyamine, or polymeric polyamine dispersants with such reagents as urea, thiourea, carbon disulfide, aldehydes, ketones, carboxylic acids, hydrocarbon-substituted succinic anhydrides, nitriles, epoxides, boron compounds, and phosphorus compounds. Such products are described in U.S. Pat. Nos. 3,036,003; 3,087,936; 3,200,107; 3,282,955; 3,366,569; 3,502,677; 3,639,242; 3,649,229; 3,702,757; 3,704,308; and 3,708,522.

Descriptions and methods of preparations of the above-mentioned dispersants are adequately presented in the patents cited hereinabove. Those portions of these patents which are directed to descriptions and methods of preparations are incorporated by reference herein.

There has now been found a dispersant that provides good dispersant properties and is compatible with the fluorohydrocarbon compositions of the newer fluorohydrocarbon engine seals. This dispersant, a high-nitrogen dispersant, is rich in alkyl bis-3-amino-1,2,4-triazole, i.e., it contains a sufficient amount of an alkyl bis-3-amino,1,2,4-triazole to be compatible with the fluorohydrocarbon elastomers. The dispersant is prepared by reacting an alkyl-substituted dicarboxylic acid compound selected from the group consisting of alkyl-substituted dicarboxylic acids, alkyl-substituted dicarboxylic acid anhydrides, and mixtures thereof, such as a polybutenyl succinic acid compound, e.g., polybutenyl succinic anhydride (PSA), and a basic salt of aminoguanidine, e.g. aminoguanidine bicarbonate (AGB), in specific amounts to form a mixture of products. When PSA is reacted with AGB, the principal product is polybutenyl bis-3-amino-1,2,4-triazole. Apparently, the aromatic character of the triazole ring reduces sufficiently the basicity of the amine, even though a high-nitrogen content is present, in order that the dispersant and the fluorohydrocarbon composition are sufficiently compatible for concurrent use in internal combustion engines.

According to the present invention, there is provided an improved process for preparing an oil-soluble composition which is suitable for use as a dispersant additive for oils of lubricating viscosity, which process comprises reacting an alkyl-substituted dicarboxylic acid compound selected from the group consisting of alkyl-substituted dicarboxylic acids, alkyl-substituted dicarboxylic acid anhydrides, and mixtures thereof with a basic salt of aminoguanidine under conditions that will provide a product that is compatible with fluorohydrocarbon elastomers and that is rich in alkyl bis-3-amino-1,2,4-triazole. More particularly, there is provided an improved process for preparing an oil-soluble composition which is suitable for use as a dispersant additive for oils of lubricating viscosity, which process comprises reacting a polybutenyl succinic acid compound selected from the group consisting of polybutenyl succinic acid, polybutenyl succinic anhydride, and mixtures thereof with a basic salt of aminoguanidine under conditions that will provide a product that is compatible with fluorohydrocarbon elastomers and that is rich in polybutenyl bis-3-amino-1,2,4-triazole.

There is provided also a lubricating oil composition, which composition comprises an oil of lubricating viscosity and a minor amount of a dispersant that is rich in an alkyl bis-3-amino-1,2,4-triazole, said dispersant being the reaction product obtained by reacting an alkyl-substituted dicarboxylic acid compound selected from the group consisting of alkyl-substituted dicarboxylic acids, alkyl-substituted dicarboxylic acid anhydrides, and mixtures thereof with a basic salt of aminoguanidine under conditions that will provide a product that is rich in said alkyl bis-3-amino-1,2,4-triazole.

A minor amount of the dispersant of the present invention is in amount that is within the range of about 0.001 wt% to about 10 wt%, based on the weight of the lubricating oil composition. Preferably, the amount is within the range of about 1 wt% to about 7 wt% (based on a 40 to 50% active solution of the dispersant in diluent oil) and, more preferably, the amount is within the range of about 2 wt% to about 5 wt% of 40 to 50% active dispersant, based on the weight of the lubricating oil composition. For purposes of the invention, a 40 to 50% active dispersant means a dispersant/oil solution containing about 40 to 50 wt% of actual dispersant, the remainder being diluent oil.

The phrase "rich in an alkyl bis-3-amino-1,2,4-triazole" means that the alkyl bis-3-amino-1,2,4-triazole is present in an amount that is sufficient to provide at least some dispersancy properties.

One of the reactants employed in the process of the present invention is an alkyl-substituted dicarboxylic acid compound selected from the group consisting of alkyl-substituted dicarboxylic acids, alkyl-substituted dicarboxylic acid anhydrides, and mixtures thereof. Such substituted dicarboxylic acid compound is prepared normally by the alkylation of an unsaturated acid, an anhydride of such acid, or a mixture thereof, the homopolymers and interpolymers of polymerizable olefin monomers containing up to about 10 carbon atoms. Such polymers are produced typically from ethylene, propylene, 1-butene, 2-butene, isobutene, 1-hexene, or 1-octene and have at least 30 carbon atoms in a chain. Preferred polymers are polybutenes. Suitable polybutenes can be purchased from Amoco Chemical Company under the INDOPOL trade name. Polypropene can be obtained from Amoco Petroleum Additives Company. The alkyl radical can be any oil-solubilizing organic radical. For example, it can be any hydrocarbon group having from 1 to 200 carbon atoms, saturated or unsaturated. It can be an alkenyl group derived from polyisobutylene of molecular weight in the range of 250 to 5000. It can be an alkenyl group derived from polypropylene or polyethylene of molecular weight in the range of 200 to 5000. It can be alkyl groups derived from the "dimer acids" or dimerized fatty acids having carbon atoms within the range of 8 to 30 carbon atoms, some acids of which may contain unsaturation. It can be an alkyl group derived from linear or branched alkenes having from 4 to 30 carbon atoms, for example, n-dodecyl, t-dodecyl, t-nonyl, or t-octyl.

Typically, the chain of carbon atoms in the substituent ranges from about 30 carbon atoms to about 200 carbon atoms, or higher; preferably, from about 50 carbon atoms to about 200 carbon atoms; and, more preferably, from about 60 carbon atoms to about 160 carbon atoms.

The acids that are contemplated for use in making the dicarboxylic acid compounds are unsaturated. Such acids and derivatives thereof as acrylic acid, methacrylic acid, maleic acid, maleic anhydride, citraconic acid, and citraconic anhydride are contemplated. The acid that is employed, when used in a specific ratio of its amount to the amount of AGB, must provide a final product that is rich in alkyl bis-3-amino,1,2,4-triazole. A preferred dicarboxylic acid and its anhydride are succinic acid and succinic anhydride.

For convenience only, the following discussion will be directed to the use of polybutenyl succinic anhydride (PSA) as the alkyl-substituted dicarboxylic acid compound. The PSA was reacted with aminoguanidine bicarbonate (AGB) in the examples which are discussed hereinafter. It will be shown that the reaction between PSA and AGB was conducted at more than one relative ratio of reactants. The products were examined for their infrared spectra and for their dispersant properties in various dispersant tests and their dispersant performances were compared to the performance of a commercial Mannich dispersant.

In one instance, one mole of PSA was reacted with one mole of AGB. The resulting product produced an infrared spectrum having a dominant peak at 1735 cm$^{-1}$ with a shoulder at 1700 cm$^{-1}$. The dispersant tests demonstrated that this product did not perform as well as the commercial Mannich dispersant.

On the other and, when one mole of PSA was reacted with two moles of AGB, the product presented an infrared spectrum having a dominant peak at 1640 cm$^{-1}$, smaller peaks at approximately 1700 cm$^{-1}$, and characteristic "N-H" stretching bands at 3200-3500 cm$^{-1}$. This product performed as well as the commercial Mannich dispersant did. The use of spectra of known compounds resulted in the revelation that the product was principally a triazole. The stoichiometry would suggest primarily a bistriazole having the following structure:

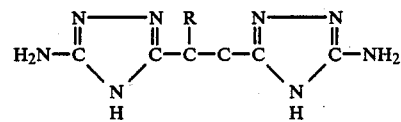

This structure is that of polybutenyl bis-3-amino-1,2,4-triazole. Such a product contains a relatively high nitrogen content, within the range of about 1.8 wt% to about 2.9 wt% nitrogen, when compared to that of the commercial Mannich dispersant, namely, 1.15 wt% nitrogen.

The five-membered ring of the triazoles is considered to be aromatic. Depending upon the salt formed, the aminotriazole will exhibit both acidic and basic properties. The aminotriazoles are fairly stable to oxidizing agents and are extremely resistant to hydrolysis.

With no intention of being bound, it is proposed that the reaction of one mole of PSA with two moles of AGB will result in the formation of a diamide, which can be seen in the infrared spectrum at the early stages of the reaction. In the presence of base, i.e., the carbonate, cyclization can occur easily to the five-membered triazole ring. During the cyclization, water and carbon dioxide are evolved.

The desired product can be obtained conveniently by reacting PSA and AGB in appropriate amounts at a temperature within the range of about 155° C. (311° F.) to about 200° C. (392° F.), preferably, within the range of about 170° C. (338° F.) to about 190° C. (374° F.), and at atmospheric pressure. Of course, the reaction could be carried out at subatmospheric pressure or superatmospheric pressure. In either case, the range of temperatures would be different from those listed for the reaction that is carried out at atmospheric pressure. The ratio of reactants is within the range of about 1.6 moles of AGB per mole of PSA to about 2 moles of AGB per mole of PSA, preferably, within the range of about 1.7 moles of AGB per mole of PSA to about 2 moles of AGB per mole of PSA. The reaction is carried out for a period of time within the range of about 1 hour to about 4 hours, preferably, within the range of about 2 hours to about 4 hours.

The polybutenyl succinic anhydride can be prepared by reacting maleic anhydride with a high molecular weight olefin or a chlorinated hydrocarbon, such as an olefin polymer of 1-butene or 2-butene, at a temperature within the range of about 100° C. (212° F.) to about 200° C. (392° F.).

The aminoguanidine and its bicarbonate salt can be obtained from commercial suppliers. For example, the aminoguanidine bicarbonate salt can be obtained from Nippon Carbide Industries Co., Inc.

The following examples are being presented to aid in the understanding of the present invention. They are being presented for the purpose of illustration only and are not intended to limit the scope of the present invention.

EXAMPLE 1

In this example, an embodiment of the dispersant of the present invention was prepared. Into a three-liter, three-necked, round-bottom flask, 1000 gpm of 57.5% active polybutenyl succinic anhydride (0.25 mole), 69.9 gm of 98.5% aminoguanidine bicarbonate (0.50 mole), and 494 gm of a 100 neutral base oil were placed under nitrogen. The polybutenyl succinic anhydride had been prepared by reacting maleic anhydride with an H-1500 INDOPOL polybutenes having a number average molecular weight ($M_n$) of about 2060, obtained from Amoco Chemical Company. The mixture under constant stirring was heated for three hours at a temperature of 188° C. (370° F.) to form the polybutenyl bis-3-amino-1,2,4-triazole. The product was filtered to provide a 40% active polybutenyl bis-3-amino-1,2,4-triazole dispersant, identified hereinafter as Dispersant No. 1.

In a similar manner, a second embodiment of the dispersant of the present invention was prepared. In this preparation, the polybutenyl succinic anhydride was prepared by reacting maleic anhydride with H-300 INDOPOL polybutenes having a $M_n$ of about 1290 and obtained from Amoco Chemical Company. This polybutenyl bis-3-amino-1,2,4-triazole dispersant is identified hereinafter as Dispersant No. 2.

Each of these two dispersants was tested in both the spot dispersancy test (SDT) and the oil thickening spot dispersancy test [OTT(SDT)]. Each of these tests measures the ability of a dispersant to suspend and move sludge chromatographically along blotter paper. For comparison, a typical commercial Mannich dispersant, identified hereinafter as Dispersant No. 3, was also subjected to these tests. The results of these tests are presented hereinbelow in Table I.

TABLE I

| Dispersant | Dispersant Performance | | | | | | | |
|---|---|---|---|---|---|---|---|---|
| | SDT % | | | | OTT (SDT) Time, hr | | | |
| | 0 | 2 | 4 | 6 | 24 | 48 | 56 | 72 |
| 1 | 37 | 46 | 85 | 84 | 100 | 93 | 90 | 42 |
| 2 | 37 | 58 | 85 | 86 | 100 | 90 | 75 | 34 |
| 3 | 37 | 60 | 84 | 88 | 100 | 88 | 69 | 28 |

These results indicate that the two embodiments of the dispersant of the present invention perform in the SDT and OTT in a manner similar to that of the reference Mannich dispersant.

EXAMPLE 2

In this example, two embodiments of the dispersant of the present invention were tested for their compatibility with Viton fluorohydrocarbon elastomers. Viton fluorohydrocarbon elastomers can be used as crankshaft seals in engines and clutch plate liners in transmissions.

Caterpillar Tractor Company of Peoria, Ill., U.S.A., has developed an experimental test for evaluating the compatibility of such elastomers and an oil containing a dispersant. According to this test, three elastomer specimens are submersed in a candidate oil for 10 days at a temperature of 149° C. (300° F.). The average percent elongation measurement represents a loss of flexibility of the Viton material. A lower value indicates a more flexible material which has resisted attack by the oil. The higher the value, the less flexible the sample. Caterpillar has established a passing oil and a failing oil to be used as references or standards for discriminating between and evaluating the candidate oils.

A conventional SF/CD heavy duty oil, identified hereinafter as Oil No. 1, was used in these tests. The dispersants were tested at a 5.5 wt% level. This oil contained Paratone 715, a non-dispersant VI improver, obtained from Paramins, a division of Exxon Corporation, in an amount of 6.9 wt%. The heavy duty oil, Oil No. 1, was tested without dispersants to demonstrate its contribution to incompatibility.

Both the Caterpillar passing oil, identified hereinafter as Oil No. 2, and the Caterpillar failing oil, identified hereinafter as Oil No. 3, were tested for their compatibility with the Viton elastomers.

In addition, two oil samples contained a third embodiment of the dispersant of the present invention, Dispersant No. 4, which third embodiment was prepared from H-300 INDOPOL polybutenes which were obtained from Amoco Chemical Company and had a $M_n$ of about 1290, and two oil samples contained a fourth embodiment of the dispersant of the present invention, Dispersant No. 5, which fourth embodiment was prepared from H-1500 INDOPOL polybutenes which were obtained from Amoco Chemical Company and had a $M_n$ of 2060. Two of these latter four samples also contained boron in the form of 0.45 wt% amylpolyborate. Each of the samples involving Oil No. 1 contained 6.9 wt% VI improver Paratone 715, obtained from Paramins, a division of Exxon Corporation.

The results of these tests are presented in Table II hereinbelow.

TABLE II

Caterpillar Viton Compatibility Tests

| Oil No. | Dispersant, 5.5 wt % | Amylpolyborate, wt % | % Elongation |
|---|---|---|---|
| 1 | — | — | 12 |
| 2 | — | — | 25 |
| 3 | — | — | 46 |
| 1 | 4 | — | 26 |
| 1 | 4 | 0.45 | 20 |
| 1 | 5 | — | 22 |
| 1 | 5 | 0.45 | 16 |

These data demonstrate that both Dispersant No. 4 and Dispersant No. 5 provided % elongations that were quite similar to that furnished by the Caterpillar passing oil reference, Oil No. 2. The addition of boron resulted in an improvement in the % elongation, i.e., a reduction in the % elongation. Consequently, either Dispersant No. 4 or Dispersant No. 5 shows good compatibility with Viton seals in the Caterpillar test, with or without boron.

EXAMPLE 3

In this example, tests were conducted to show the necessity of using basic aminoguanidine to prepare the dispersants of the present invention. Samples of dispersants were prepared by reacting polybutenyl succinic anhydride with either aminoguanidine bicarbonate (AGB), obtained from Aldrich Chemical Co., or aminoguanidine nitrate (AGN), obtained from Aldrich Chemical Co. or aminoguanidine hemisulfate (AGH), obtained from Eastman Kodak Co. The preparations of the polybutenyl succinic anhydrides and the resulting dispersant products were conducted as described hereinabove. The polybutenyl succinic anhydrides were either PSA-1, which were prepared from H-300 INDOPOL polybutenes which were obtained from Amoco Chemical Company and had a $M_n$ of about 1290, or PSA-2, which were prepared from H-1500 INDOPOL polybutenes which were obtained from Amoco Chemical Company and had a $M_n$ of about 2060. Dispersant products were obtained by reacting one mole of PSA-1 with one mole of AGB (Dispersant No. 6), one mole of PSA-1 with two moles of AGN (Dispersant No. 7), one mole of PSA-1 with PSA-1 with two moles of AGH (Dispersant No. 8), one mole of PSA-1 with two moles of AGB (Dispersant No. 9), one mole of PSA-2 with one mole of AGB (Dispersant No. 10), and mole mole of PSA-2 with two moles of AGB (Dispersant No. 11). A typical Mannich dispersant (Dispersant No. 12) was used as a reference.

Each of the resulting dispersant products was subjected to the spot dispersancy test (SDT) and to the oil thickening test (OTT). The spot dispersancy test measures the movement of insoluble particles chromatographically along blotter paper in used motor oil. When a dispersant candidate is used oil, movement along the paper results in two rings. The inner ring constitutes the sludge being transported by the dispersant; the outer ring comprises the base oil. The effectiveness of the dispersant is defined by the ratio of the inner ring to the outer ring. The higher the value of this ratio for a particular candidate, the better the performance of that candidate as a dispersant. The oil thickening test is an analogous test in which the dispersant is tested in an oil that is being oxidized and the spot dispersancy test indicates the effect of this oxidation with time.

The results of the spot dispersancy tests are presented hereinbelow in Table III. The results of the oil thickening tests are presented hereinbelow in Table IV.

TABLE III

| Spot Dispersancy Test Results | | | | | | | |
|---|---|---|---|---|---|---|---|
| Dispersant Product No. | PSA Type | AG Salt[1] Moles | Type | Wt % Dispersant 0 | 2 | 4 | 6 |
| 6 | PSA-1 | 1 | AGB | 35 | 43 | 58 | 71 |
| 7 | PSA-1 | 2 | AGN | 35 | 39 | 43 | 63 |
| 8 | PSA-1 | 2 | AGH | 35 | 39 | 41 | 55 |
| 9 | PSA-1 | 2 | AGB | 35 | 49 | 84 | 92 |
| 10 | PSA-2 | 1 | AGB | 35 | 42 | 46 | 66 |
| 11 | PSA-2 | 2 | AGB | 35 | 56 | 82 | 87 |
| 12 | — | — | — | 35 | 54 | 76 | 88 |

[1]AG Salt = aminoguanidine salt.

TABLE IV

| Oil Thickening Test Results | | | | | | | | |
|---|---|---|---|---|---|---|---|---|
| Dispersant Product No. | PSA Type | AG Salt[1] Moles | Type | Time, hr 24 | 48 | 56 | 72 | 80 |
| 6 | PSA-1 | 1 | AGB | 100 | 85 | 73 | 31 | — |
| 9 | PSA-1 | 2 | AGB | 100 | 90 | 75 | 34 | — |
| 10 | PSA-2 | 1 | AGB | 100 | 89 | 87 | 47 | 41 |
| 11 | PSA-2 | 2 | AGB | 100 | 93 | 90 | 42 | — |
| 12 | — | — | — | 100 | 88 | 69 | 28 | 30 |

[1]AG Salt = aminoguanidine salt.

The results presented in Table III show that a product prepared with one mole of aminoguanidine bicarbonate per mole of PSA, or a product prepared with two moles of aminquanidine nitrate per mole of PSA, or a product prepared with two moles of aminoguanidine hemisulfate per mole of PSA does not provide a response equivalent to that of Dispersant No. 12, the typical Mannich dispersant. The use of two moles of aminoguanidine bicarbonate per mole of PSA when using either type of PSA did give a response that is equivalent to the response provided by the reference Mannich dispersant. In addition, there was no great distinction between responses provided by the bistriazole products prepared from either PSA at equal weight.

The results presented in Table IV demonstrate that the products prepared from either one mole or two moles of aminoguanidine bicarbonate per mole of PSA furnished OTT responses that were not appreciably different from the response provided by the reference Mannich dispersant. Hence, the oxidation of these products is similar to that of the reference Mannich dispersant.

EXAMPLE 4

In this example, samples of products were prepared from aminoguanidine bicarbonate obtained from two sources. Some were prepared from aminoguanidine bicarbonate obtained from Aldrich Chemical Company. This material was 98.5% pure. Other samples were prepared from aminoguanidine bicarbonate obtained from Nippon Carbide Industries Co., Inc. This material was either 99.7% or 92.9% pure amine. Reactions were conducted with each of the three specimens of aminoguanidine bicarbonate at AGB:PSA ratios of 1.9:1 for 1:1 for both PSA-1 and PSA-2. The 92.9% aminoguanidine bicarbonate, which contained approximately 7% water caused a great deal more foaming during the reaction than the others. Nitrogen content (Dumas) and viscosity were determined for each product. Spot dispersancy tests were conducted for each dispersant product. The Mannich dispersant was used again as a reference. The results of these tests are presented hereinafter in Table V.

these motored engine tests are presented hereinbelow in Table VI.

TABLE V

Effect of AGB Source and Amount on SDT

| PSA Type | AGB Source | AGB Purity, % | AGB:PSA | Viscosity, cSt | N, % | SDT wt % Dispersant 0 | 2 | 4 | 6 |
|---|---|---|---|---|---|---|---|---|---|
| PSA-1 | A(1) | 98.5 | 1:1 | 183 | 1.97 | 39 | 39 | 60 | 72 |
| PSA-1 | N(2) | 99.7 | 1:1 | 176 | 1.99 | 39 | 40 | 59 | 71 |
| PSA-1 | N | 92.9 | 1:1 | 176 | 1.87 | 39 | 40 | 63 | 71 |
| PSA-1 | A | 98.5 | 1.9:1 | 190 | 2.97 | 39 | 55 | 76 | 79 |
| PSA-1 | N | 99.7 | 1.9:1 | 205 | 2.98 | 39 | 61 | 72 | 80 |
| PSA-1 | N | 92.9 | 1.9:1 | 185 | 3.06 | 39 | 55 | 76 | 83 |
| PSA-2 | A | 98.5 | 1:1 | 454 | 0.98 | 39 | 45 | 44 | 60 |
| PSA-2 | N | 99.7 | 1:1 | 480 | 1.19 | 39 | 40 | 47 | 67 |
| PSA-2 | N | 92.9 | 1:1 | 463 | 1.02 | 39 | 37 | 51 | 73 |
| PSA-2 | A | 98.5 | 1.9:1 | 516 | 1.95 | 39 | 59 | 74 | 78 |
| PSA-2 | N | 99.7 | 1.9:1 | 536 | 1.74 | 39 | 57 | 74 | 80 |
| PSA-2 | N | 92.9 | 1.9:1 | 490 | 1.94 | 39 | 62 | 77 | 80 |
| MANNICH DISPERSANT | — | — | — | — | 1.15 | 39 | — | 79 | — |

(1) A = Aldrich Chemical Company
(2) N = Nippon Carbide Industries Co., Inc.

The data in this table suggest that the nitrogen content is consistent within each type of product. For example, the bis-triazole dispersants made with PSA-1 and at an AGB:PSA ratio of 1.9:1 h ave a nitrogen content of approximately 3 % regardless of the source of aminoguanidine bicarbonate. The viscosities of the products are similar, varying with the molecular weight of PSA employed. FOr a particular molecular weight of PSA, the viscosities are slightly higher when a larger ratio of AGB to PSA is used. The spot dispersancy tests discriminated between the type of product prepared (AGB:PSA molar ratio); however, they did not show any appreciable differences in the products obtained from AGB's having different sources. In addition, infrared spectra obtained on the dispersants prepared from PSA-1 showed very little differences, suggesting that the same product was being prepared regardless of the source of AGB.

EXAMPLE 5

In this example, the friction modification properties of an embodiment of the dispersant of the present invention were evaluated. The embodiment was prepared by reacting PSA-1 with AGB as described hereinabove. This embodiment is identified hereinafter as Dispersant No. 13. It was compared with a typical Mannich dispersant prepared from H-300 INDOPOL polybutenes obtained from Amoco Chemical Company and having a $M_n$ of about 1290, Dispersant No. 14.

Oils containing the dispersants were prepared to the same viscosities. Each oil sample was made up of a solvent-extracted, 20 weight, Gulf Canada base stock, Oil No. 4, 4.0 wt% dispersant, 1.0 wt% zinc dialkyldithiophosphate inhibitor, 1.2 wt% high-base magnesium sulfonate rust inhibitor, and 0.08 wt% copper carboxylate. These were SAE 20 straight grade oils, since viscosity effects that are present in multigrade oils would mask friction effects in the boundary area.

The friction modification properties of each oil were evaluated in a motored engine test. The base line oil used in these tests was a 10W40 multigrade oil, "LDO", obtained from Amoco Oil Company. This base line oil was assigned arbitrarily a percent improvement of zero in the boundary friction area. The experimental oils were then measured as positive or negative in relation to "LDO" in the boundary friction area. The results of

TABLE VI

| | Motored Engine Tests | | |
|---|---|---|---|
| Oil | Dispersant | Grade | Boundary Friction Area % Improvement |
| LDO | — | 10W40 | 0 |
| 4 | 13 | 20 | −20 to −40 |
| 4 | 14 | 20 | .9 |

These results demonstrate that the oil containing the embodiment of the dispersant of the present invention provided a marked improvement in the boundary friction area of the motored engine over the oil containing the typical Mannich dispersant. Directionally, the embodiment of the dispersant of the present invention appears to contribute to friction modification in a motor oil. It appears to be even better than the 10W40 oil, "LDO," which has the added benefit of viscosity properties for friction modification.

The dispersant product of the present invention can be used suitably as a lubricating oil dispersant additive composition. It not only performs satisfactorily in the spot dispersancy test and the oil thickening spot dispersancy test, as shown by Example 1, but also is compatible with fluorohydrocarbon elastomers, as demonstrated by Example 2, and provides friction modification properties to the oil to which it is added, as shown by Example 5.

What is claimed is:

1. A process for preparing an oil soluble composition which is suitable for use as a lube oil dispersant additive having improved compatibility with fluorohydrocarbon-containing elastomeric engine seals, which process comprising reacting a hydrocarbyl substituted dicarboxylic compound selected from the group consisting of hydrocarbyl-substituted dicarboxylic acids, hydrocarbyl-substituted dicarboxylic acid anhydrides, and mixtures thereof, said hydrocarbyl substituent being about $C_{30}$–$C_{200}$, with a basic salt of aminoguanidine, wherein said reaction is conducted at a temperature of from about 170° C. (338° F.) to about 200° C. (392° F.) and the relative amounts of said aminoguanidine and said hydrocarbyl substituted dicarboxylic compound are such that the product obtained upon reaction thereof exhibits of dominant infrared peak at 1640 cm$^{-1}$.

2. The process of claim 1, wherein said hydrocarbyl substituted dicarboxylic compound is the reaction product of maleic anhydride and polybutene.

3. The process of claim 2 wherein said hydrocarbyl substituted dicarboxylic compound is polybutenyl succinic anhydride and said basic salt of aminoguanidine is aminoguanidine bicarbonate.

4. The process of claim 2, wherein said reaction temperature is within the range of about 170° C. (338° F.) to about 190° C. (374° F.).

5. The process of claim 4, wherein said reaction is conducted for about 2 hr. to about 4 hr.

6. A dispersant composition comprising: the reaction product obtained upon reacting a hydrocarbyl substituted dicarboxylic compound selected from the group consisting of hydrocarbyl substituted dicarboxylic acids, hydrocarbyl substituted dicarboxylic acid anhydrides, and mixtures thereof, said hydrocarbyl substituent being about $C_{30}$–$C_{200}$, with a basic salt of aminoguanidine at a temperature of from about 170° C. (338° F.) to about 200° C. (392° F.), said reaction product being characterized by a dominant infrared peak at 1640 cm$^{-1}$.

7. The dispersant composition of claim 6 wherein said hydrocarbyl substituted dicarboxylic compound is the reaction product of maleic anhydride and polybutene.

8. The dispersant composition of claim 7 wherein said hydrocarbyl substituted dicarboxylic compound is polybutenyl succinic anhydride and said basic salt of aminoguanidine is aminoguanidine bicarbonate.

9. The dispersant composition of claim 8 wherein the polybutenyl succinic anhydride and aminoguanidine bicarbonate are reacted at a temperature of about 170° C. (338° F.) to about 190° C. (374° F.).

10. A composition comprising lubricating oil and a dispersant additive, said dispersant additive comprising: the reaction product obtained upon reacting a hydrocarbyl substituted dicarboxylic compound selected from the group consisting of hydrocarbyl substituted dicarboxylic acids, hydrocarbyl substituted dicarboxylic acid anhydrides, and mixtures thereof, said hydrocarbyl substituent being about $C_{30}$–$C_{200}$, with a basic salt of aminoguanidine at a temperature of from about 170° C. (338° F.) to about 200° C. (392° F.), said reaction product being characterized by a dominant infrared peak at 1640 cm$^{-1}$.

11. The lubricating composition of claim 10 wherein said hydrocarbyl substituted dicarboxylic compound is the reaction product of maleic anhydride and polybutene.

12. The lubricating composition of claim 11 wherein said hydrocarbyl substituted dicarboxylic compound is polybutenyl succinic anhydride and said basic salt of aminoguanidine is aminoguanidine bicarbonate.

13. The lubricating composition of claim 12 wherein the polybutenyl succinic anhydride and aminoguanidine bicarbonate are reacted at a temperature of about 170° C. (338° F.) to about 190° C. (374° F.).

* * * * *